United States Patent [19]
Baumuller

[11] Patent Number: 6,033,354
[45] Date of Patent: Mar. 7, 2000

[54] PULLING ACTION SEPARATOR

[75] Inventor: Théodore Baumuller, Schweighouse-Sur-Moder, France

[73] Assignee: Naturembal (S.A.), Bouxwiller, France

[21] Appl. No.: 08/952,816

[22] PCT Filed: May 29, 1996

[86] PCT No.: PCT/FR96/00805

§ 371 Date: Mar. 27, 1998

§ 102(e) Date: Mar. 27, 1998

[87] PCT Pub. No.: WO96/38272

PCT Pub. Date: Dec. 5, 1996

[30] Foreign Application Priority Data

May 31, 1995 [FR] France .................................. 95-06675

[51] Int. Cl.$^7$ ........................................................ B31B 1/00
[52] U.S. Cl. ........................ 493/464; 493/372; 493/967; 83/282
[58] Field of Search ..................................... 493/464, 967, 493/363, 364, 366, 372, 476, 477; 83/282, 382, 456, 627, 630

[56] References Cited

U.S. PATENT DOCUMENTS

| | | |
|---|---|---|
| 3,895,751 | 7/1975 | Shepherd, III . |
| 4,601,225 | 7/1986 | Starnes et al. ............................ 83/282 |
| 4,699,609 | 10/1987 | Komaransky et al. . |
| 4,717,613 | 1/1988 | Ottaviano ................................ 493/967 |
| 5,107,732 | 4/1992 | Hanmer .................................... 83/175 |
| 5,123,889 | 6/1992 | Armington et al. . |
| 5,213,867 | 5/1993 | Huston, Sr. et al. . |
| 5,569,146 | 10/1996 | Simmons ................................. 493/464 |

FOREIGN PATENT DOCUMENTS

| | | |
|---|---|---|
| 91839 | 5/1994 | Finland . |
| 247660 | 6/1912 | Germany . |

*Primary Examiner*—John Sipos
*Assistant Examiner*—Steven Jensen
*Attorney, Agent, or Firm*—Wood, Herron & Evans, L.L.P.

[57] ABSTRACT

A separator for cutting a cushioning/packing material generally in the form of a continuous web made from a base stock of stacked paper sheets, crushed so as to form a cushioning web which moves along a conveyance axis (A) orthogonal to the separator, is characterised in that it includes means for pulling off the portion downstream from said separator, which means operate by a tearing off action exerted at right angles from the conveyance axis (A) and further have means (2, 2', 3, 3') for securely holding the web material in a stationary position at least in the pulling off region, while the tearing means (4) act upon the web material to separate the portion downstream from said separator.

14 Claims, 5 Drawing Sheets

PULLING ACTION SEPARATOR

FIELD OF THE INVENTION

This invention relates to a parting device designed to sever a material having generally the shape of a continuous band in displacement along an axis perpendicular to said device, and operating by tearing off each successive section. The invention relates also to the machines equipped with said device, a method for its operation, as well as the obtained products.

BACKGROUND OF THE INVENTION

The cushioning dunnage product obtained at the outlet of a cushioning dunnage producing machine comprises generally a resilient band with a central zone of a thickness less than the lateral edges, which have the shape of longitudinal pads or pillows. In order to use such a material in a cushioning fashion to protect various articles during shipment, sections of various lengths are required depending on the volume of the container and the dimensions of the article to be shipped therein. This is why severing devices are needed at the machine outlet.

Up to now, such devices comprised movable knives, as is described for example in U.S. Pat. Nos. 4,699,609 and 5,123,889. In the first of those patents, the cutting device is of the shearing type comprising a fixed blade and a movable blade actuated by an electric motor. The second patent is presented as an improvement to said cutting device, inasmuch as the driving means includes a combination of motor means and an usual mechanical crank-linking rod linkage to provide a better control of the successive cutting operations, by a transformation of the rotative motor means into a linear alternative displacement.

In the above mentioned patents the severing devices of the prior art are operating by a lateral shearing which therefore applies a lateral action upon the plies of the material which have been previously connected together by mechanical means imparting to said plies a rather irregular cohesion, for example by coining, corrugating or the same. The shearing efforts have for consequence to reduce the effects of this friction connection obtained upon the successive plies obtained by the above processes and can even reduce the cohesion of the product at the severed ends.

In opposition to that the severing device of the invention provides a better connection of the plies at each severed end, which has for effect to substantially improve the cohesion of the cushioning dunnage products obtained.

SUMMARY OF THE INVENTION

More specifically, according to the invention, the tearing off of successive sections of cushioning dunnage is carried out in two successive steps: in a first step, the band-like material is immobilized at least in the tearing off zone, and in a second step, the device tears through the immobilized material in a direction perpendicular to the axis of displacement of the material.

This device is particularly adapted to be used at the outlet of machines for producing cushioning dunnage materials from a band-type paper stock, formed from either single or plural plies, the lateral edges of which have been folded laterally inwardly upon the central longitudinal zone of the band, and which is then driven longitudinally, crumpled and tightly connected by successive compressions.

As explained above, the severing action of the device of the invention is obtained through tearing off means applied to the material section down stream of the device, and acting by a tearing process perpendicularly to the displacement axis of the initially continuous band of stock material. Said tearing means comprises means to tightly keep said material immobile at least in the tearing zone, whereas tearing means are acting upon it to severe the downstream section.

Said means do not act simultaneously, but at least partially in sequence, so that the tearing is carried out only when the band is immobilized. According to the invention, the severing device comprises means for repetitively and at least sequentially controlling the movement of the means keeping the band material in a fixed position and of the tearing means.

Preferably, said controlling means comprises at least a first connecting rod assembly linking the driving means to the means for keeping immobile the band material, and at least a second connecting rod assembly linking said driving means to the tearing means, said driving means imparting an alternative motion to said immobilizing means and to said tearing means.

According to a possible modification, in both cases the driving means comprises a rotative disc driven by a motor, one end of each connecting assembly being mounted pivotally at the periphery of said disc. Said disc is preferably an unique disc for both connecting assemblies, which are pivotally mounted at the same point of the periphery of the disc. Said disc is preferably driven by an electric motor, e.g. a moto-reductor.

In the system of the invention, the first connecting assembly comprises a toggle joint including three arms; one of the ends of said arms is pivotally mounted around a central axis; the other ends of said arms are pivotally mounted respectively upon the driving disc, upon a pin fixed to the frame supporting the severing device, and upon a pin fixed to the immobilizing means.

The second connecting assembly comprises two arms: the first arm has a first end pivotally mounted upon the driving disc and its second end pivotally mounted upon a pin fixed at one end of the second arm. The second arm has its first end pivotally mounted upon a pin fixed at the frame supporting the severing device, and its second end pivotally mounted upon a pin fixed to the tearing means.

When actuated by the above driving means, both connecting assemblies actuate at least partially in sequence the immobilizing means and the transversal tearing means acting upon the band.

The immobilizing means are disposed on each side of the band and facing each other with respect to the displacement plane containing the displacement axis and substantially median with regard to the band.

Preferably, said immobilizing means are movable on one side of the material, whereas they are fixed on the other side.

The movable immobilizing means are linearly guided in a plane perpendicular to the displacement plane, by grooves in which said movable immobilizing means are alternatively sliding in one direction and in the other, in order to approach, to engage and to move away from the fixed immobilizing means disposed on the other side of the band.

When said means are engaged through the material they keep therefore the material tightly held, and thus the tearing can occur. However the precise place of the severing is not of little importance and should be located in a comparatively small zone where the longitudinal strain due to the immobilizing means is the highest. In addition, the tearing action must occur perpendicularly to the displacement axis.

For this reason, the tearing means are also linearly guided in a plane perpendicular to the displacement axis, by grooves in which they slide alternatively in one direction and in the other, in order to engage the band and to initiate the subsequent tearing by tearing off.

It is clear that both linear alternative motions of the immobilizing means for the material and of the tearing means are carried out respectively by the first and the second connecting assemblies.

The above immobilizing means are preferably jaws, i.e. two on each side of the band, being spaced from each other by an interval in which the tearing means are disposed.

As explained hereunder more in detail, there exists a deep interaction between, on the one hand, the immobilizing jaws which comprise on each side two transversal surfaces designed to engage and squeeze the band to sever and, on the other hand, the tearing means which act between the pairs of jaws.

The tearing means comprise at least one plate designed to carry out a tearing perpendicularly to the displacement axis during the time when the jaws disposed on both sides of the band are engaged through the band and keep it tightly immobile.

Preferably, said tearing plate is a saw. During the movement of the plate towards the band of material tightly kept by the jaws, the sharp teeth engage the portion of band stretched between said jaws and initiate a punching which broadens as long as the interaction band/plate increases: the band material is then severed after a progressive weakening along a transversal line which ends by a tearing off when the punched holes join one another.

According to a most preferential modification, the fixed jaws provide at least partially the guiding slide for the tearing saw, which moves between them and also between the movable jaws during the tearing step. This configuration has for further advantage to guarantee the positioning of the plate transversally with respect to the portion kept immobile and stretched of the band to sever.

In operation, according to the invention, the movable jaws and the tearing plate move before an opening provided for the passage of the band material, the displacement covered being at least equal to the width of said opening. As already explained, the severing device of the invention can be used in combination with various systems for producing band material to sever. For example, such an opening can be the open outlet of a tunnel bringing the band, and disposed downstream of other sections carrying out other treatments to the band.

The fact that the motion length of the movable jaws and of the tearing plate be longer than the width of said opening prevents any dysfunctioning at the outlet; e.g. it prevents the severed section from remaining engaged with the movable jaws on the tearing "lip" as it will be described more fully hereinafter.

As a non limiting example, the device can be used with a machine for producing cushioning dunnage material from a paper stock comprising at least one web of paper, longitudinally folded inwardly towards the central area of the band, so that the edges of the band are superimposed in said central zone, then pulling the folded assembly, crumpling the folded assembly and finally connecting the crumpled assembly by successive compressions.

Such a machine is also provided by the invention and comprises a generally rectangular exit opening disposed upstream the device, through which the band material passes before the successive sections are severed.

The device is preferably fixed upon a panel in which said opening is cut, so that the movable immobilizing means and the tearing means for the band material, i.e. respectively the moving jaws and the tearing plate, slide before said opening. Such a panel can be integral with the frame or being fixed upon it.

This invention further provides a process for producing a cushioning dunnage band material obtained from a band of stock material comprising a plurality of paper webs, said process comprising the steps of: longitudinally folding the lateral edges of the band towards the central zone of the band, pulling the folded assembly, crumpling the folded assembly, and finally connecting the crumpled assembly by successive compressions, the method being characterized in that the final operation comprises severing the material into successive sections, with a severing device having means for successively tearing off each section downstream of the device, as described above.

Finally, the invention further provides a product as obtained with a machine for producing cushioning dunnage products, supplied in a band material such as single ply or multi-ply paper sheet by folding longitudinally the lateral edges of sheet stock material towards the central zone of said band, in order to superimpose said edges in said central zone, then by pulling the folded assembly, by crumpling the folded assembly and finally by connecting the crumpled assembly by successive compressions, said machine being characterized in that it comprises a tearing off device for successive sections of the band at its outlet, as described above.

As already mentioned, the major advantage of such a product relative to the prior art products is that the ends of the severed dunnage product are much more coherent, i.e. they have a higher connection strength of the several plies engaging each other. The tearing off at both ends due to the conditions by which it is obtained, imparts to the end areas some kind of stitching, due to the irregularities of the severing area and to the folding of said irregularities, giving a mutual adhesion of the plies in this zone.

BRIEF DESCRIPTION OF THE DRAWINGS OF THE INVENTION

The invention will now be described more in detail, with reference to the annexed drawing, upon which:

DETAILED DESCRIPTION OF THE INVENTION

Figure 1:
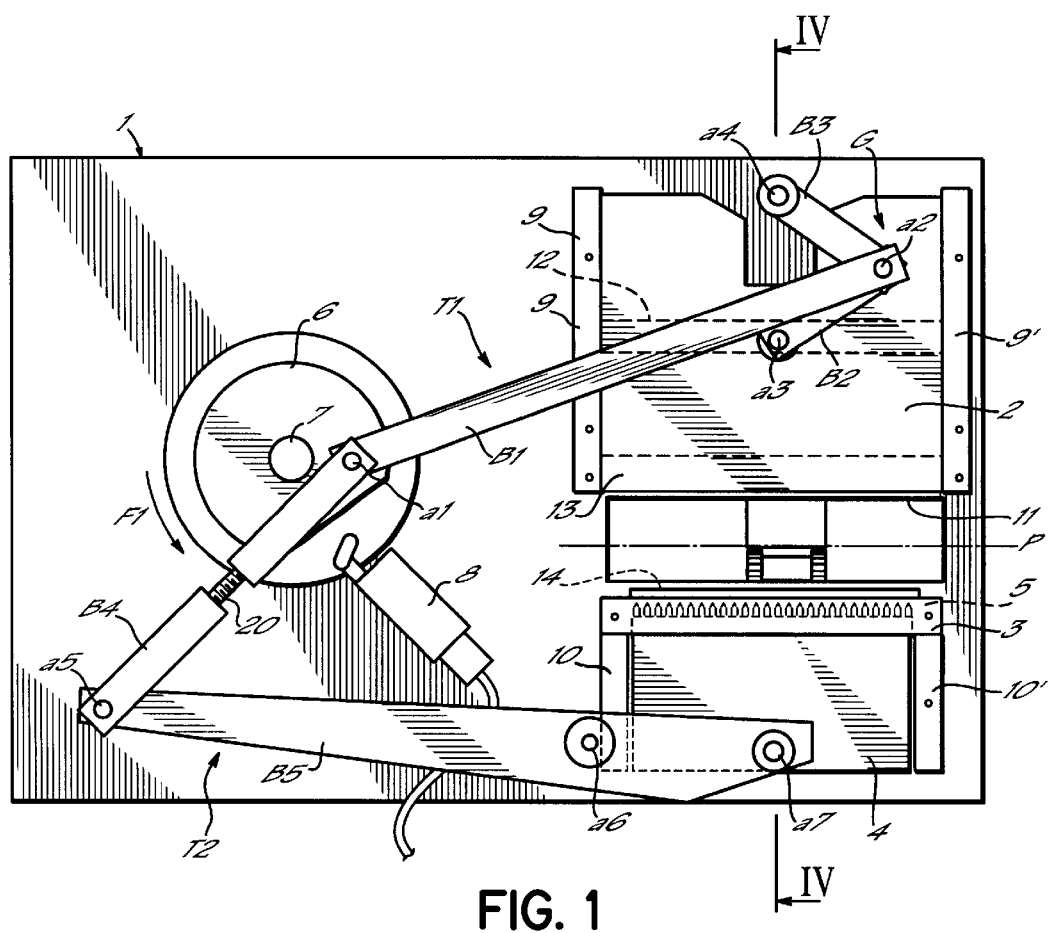
FIG. 1 is a front view of the severing device of this invention.

The device of the invention is preferably supported by a frame (1) forming itself an integral part of the machine housing, or preferably comprising a panel fixed by proper means to the housing. In the modification illustrated by FIG. 1, the severing device comprises essentially a saw (5) clearly shown in FIG. 1. The stock sheet band proceeds along a displacement axis (A) substantially in a median plane (P).

The movable jaws (2, 2') are linked to a first connecting rod assembly (T1) comprising a toggle joint (G), whereas the tearing plate (4) is linked to a second connecting rod assembly (T2), said connecting rod assemblies (T1, T2) giving the movable parts (movable jaws (2, 2') and plate (4)) a motion initiated by a driving disc (6). The latter is itself driven by driven means (not shown) by a shaft (7), said driven means being preferably an electrical moto-reductor.

An electrical moto-reductor has in fact a flexible control capacity as requested by a high degree of automation of the severing operation by tearing off, which can be repetitive at various frequencies.

The connecting rod assembly (T1) transmits the motion of the disc (6) to the movable jaws (2, 2'), the transformation of the rotative motion into a translation motion being obtained by using parallel slides (9, 9') fixed upon the frame (1). The overall system comprises four pivoting axes, corresponding each to a pin (a1, a2, a3, a4) around which the rotations occur.

The pin a1 is fixed on a peripheric zone of the disc (6) to generate a circular motion, the radius of which is equal to the distance between the axis (7) and the pin (a1). The pin (a2) is not connected to the movable jaws (2, 2'), but only to the three arms (B1, B2, B3) forming the toggle joint (G). The pin (a3) is the pivoting axis of arm (B2) upon the movable jaws (2, 2') and the pin (a4) is fixed upon the frame (1) and forms a fixed axis for the toggle joint (G). Such a system has for effect to impart to the movable jaws (2, 2') a rectilinear alternative motion with regard to the fixed jaws (3), with an engaging strength sufficient to tightly maintain the band during the severing by tearing off of sections, the precise direction of the motion being imposed by the slides (9, 9').

Figure 2:
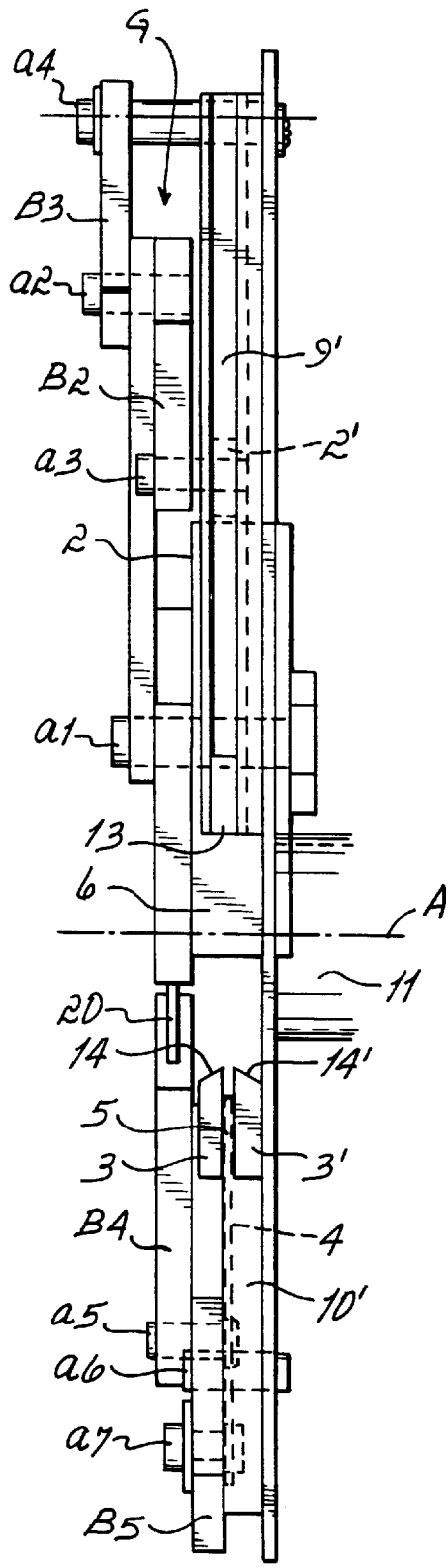
FIG. 2 is a side view of the same device.
Figure 4:
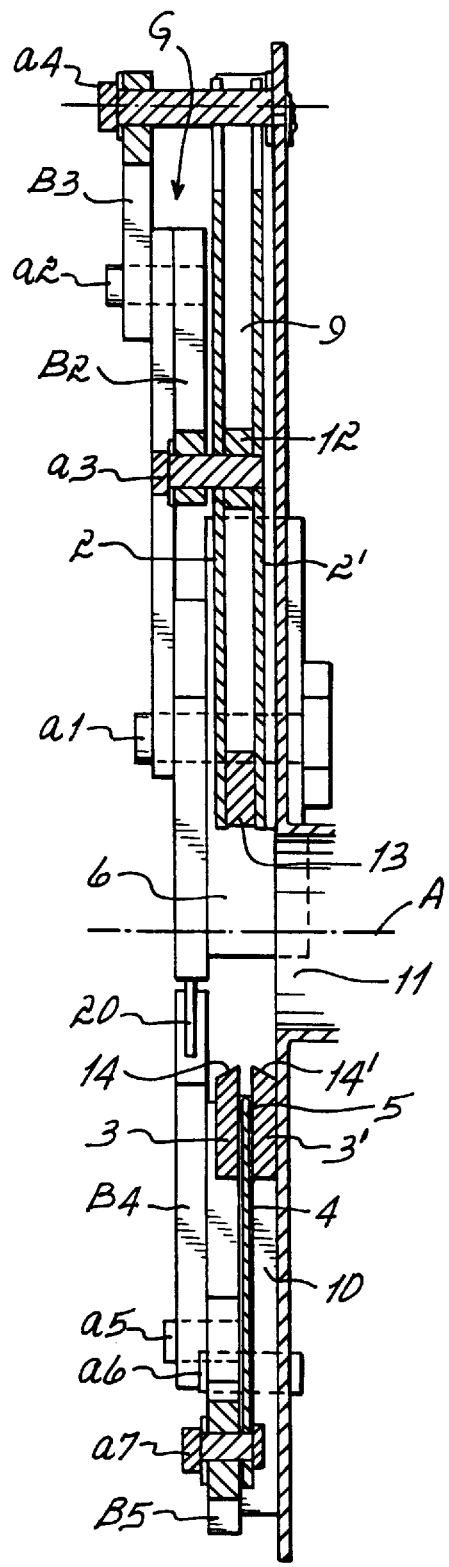
FIG. 4 is a cross section along the line 4—4 of FIG. 1, taken in the arrow direction.

It should be noted that the position of the pin (a4) is adjustable with respect to frame (1), by means of an eccentric which can be seen on FIGS. 2 and 4, in a known manner.

The connecting rod assembly (T2) functions in a similar manner: Further pins (a5, a6, a7) control the motion of arms (B4, B5) imparting also a rectilinear alternative motion to the tearing blade (4), by means of slides (10, 10'). The pivotal movement upon the disc (6) occurs around the same pin (a1) as previously described. The pin (a5) is not fixed to frame (1); the pin (a6) used as a fixed pivot for the arm (B5) is fixed to the frame (1). Finally, the pin (a7) connects the arm (B5) to the tearing plate (4) to transmit to it the motion initiated by the disc (6).

As will be explained later, both connecting rod assemblies (T1, T2) have for effect to communicate to the movable jaws (2, 2') and to the plate (4) a sequential motion, the plate acting obviously after the jaws. Both guiding slides (9, 10', 10, 10') are placed on each side of a rectangular opening (11) downstream of a central pulling and crumpling system of a machine for producing cushioning dunnage products, said opening encompassing the displacement median plane (P).

The connecting rod assemblies are adaptable to be adjusted, as for example the adjustment of the length of the arm (B4), for example by a threaded rod (20). It should also be noted that the tearing plate (4) has a width smaller than the distance between both slides (10, 10'). There occurs thus a beginning of vertical swinging of plate (4), which attacks the band with a slight slope, improving the severing action.

FIGS. 2 and 4 give a further view of the invention, by showing the device in a side view and in cross section, along lines 4—4. These Figures clearly show an essential detail of the invention: there are two pairs of jaws (2, 2', 3, 3') and the sawblade (4) moves inside the space or gap between each pair. This is very important, inasmuch as said blade (4) acts in the zone of stretching and of maximum immobilization of the band resulting from the engaging of the jaws (2, 2', 3, 3').

The pair of movable jaws comprises two parallel plates (2, 2') joined by a distance piece (12) at the level of pin (a3), leaving free the space between said plates in the vicinity of the rectangular opening (11). One additional guiding means comprises a distance piece (13) in the vicinity of said opening (11).

The pair of fixed jaws also comprises two plates (3, 3') of smaller size, sufficiently spaced for accomodating the tearing plate (4). The portion provided to engage the movable jaws (2, 2') comprises an upper tapered edge (14, 14') to allow some deflection of the plate due to their compression.

Figure 3A:
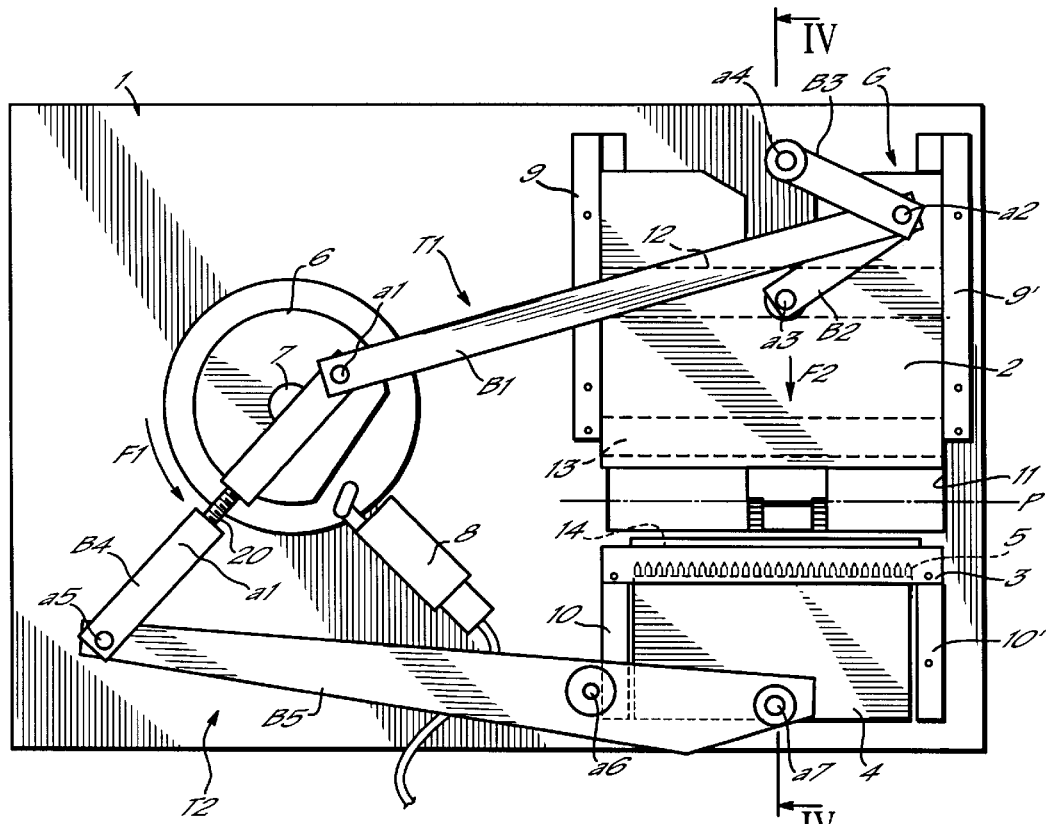
FIGS. 3a to 3d are equivalent front views showing the successive steps of the tearing off band sections.
Figure 3B:
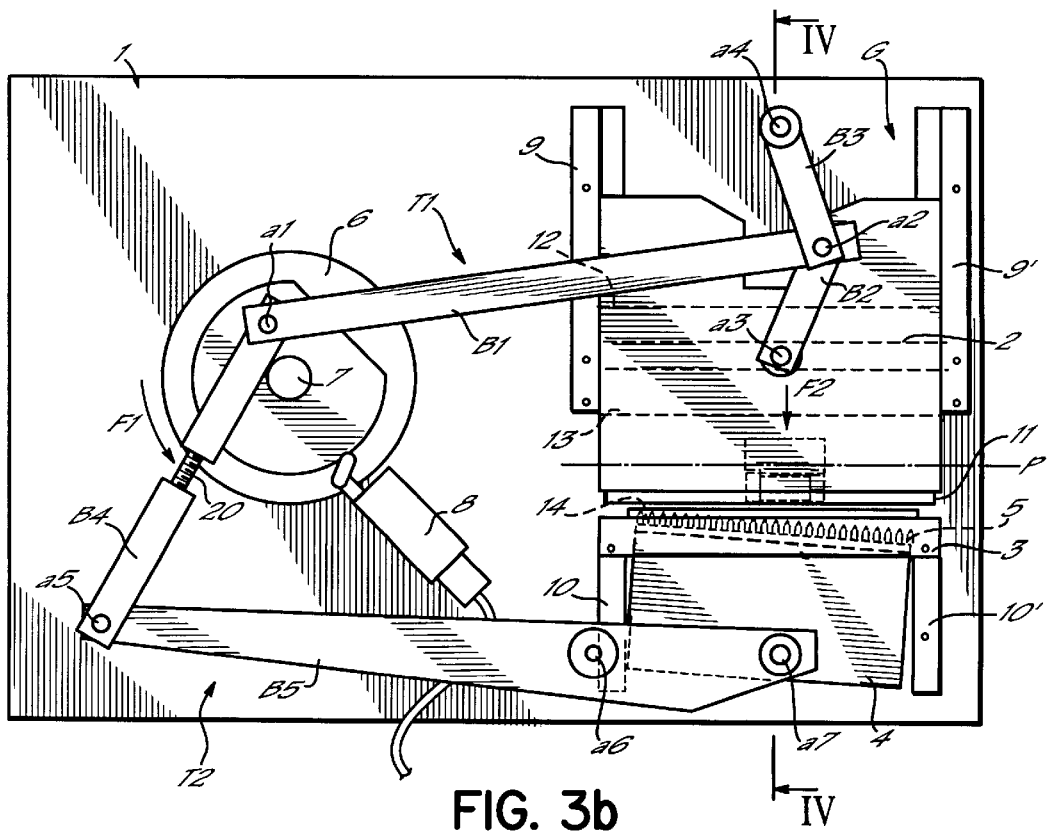
Figure 3C:
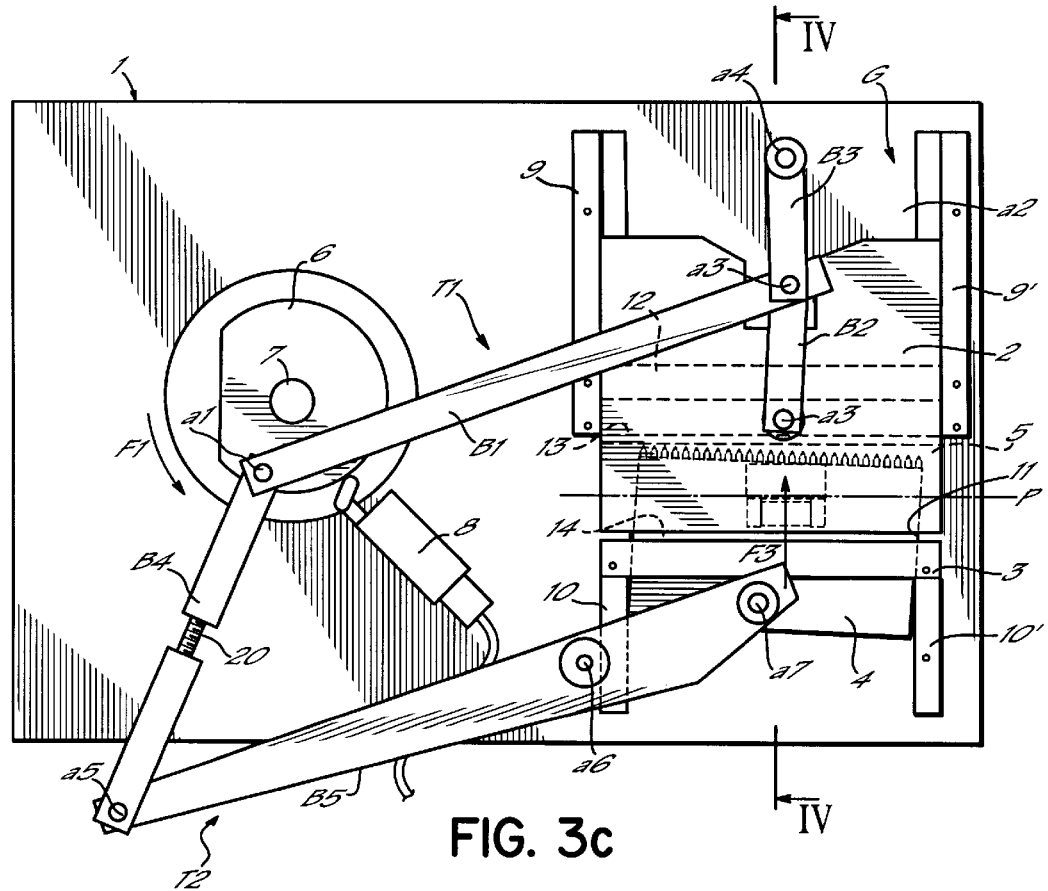
Figure 3D:
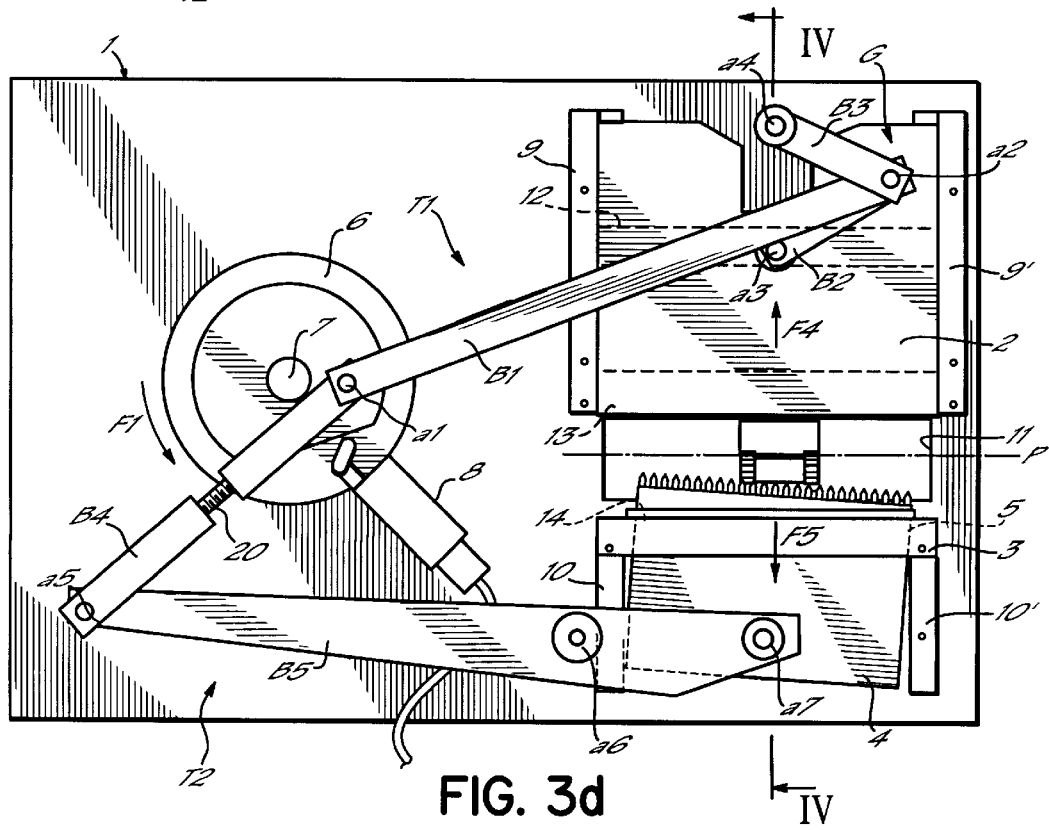

Turning now to FIGS. 3a to 3d and 5, there is shown a complete operation cycle, starting substantially at FIG. 3a and finishing substantially at FIG. 3d. In a first step, the disc (6) turning in the direction of arrow (Fl), the movable jaws (2, 2') are actuated in the direction of arrow (F2), i.e. towards the fixed jaws (3, 3'), passing before the opening (11) to reach the tapered edges (14, 14') of the fixed jaws (3, 3'), through the band to be severed, which will leave actually a very small distance between both pairs of jaws.

During this first step, the movable tearing plate (4) does practically not move, except a small initial swinging at the beginning of its rectilinear motion towards the band, as it appears in FIG. 3b.

Then the movable jaws (2, 2') remain in compressive engagement against the fixed jaws (3, 3'), immobilizing thus the band, while the plate (4) moves upwards between the movable jaws (2, 2') as shown by arrow (F3) upon FIG. 3c. It should be noted that the pressure exerted by said movable jaws (2, 2') upon the fixed jaws (3, 3') is not constant, but passes through a maximum value, which substantially corresponds to the culmination of the tearing off step. The working action of the teeth of the plate (4) occurs very progressively, the final tearing off, when the severing action is maximum, occurs at the moment when the pressure of the jaws is maximum, creating a longitudinal stretch sufficient to balance the cutting strains.

The movable jaws (2, 2') and the plate (4) move then back in the direction of arrows (F4, F5) (FIG. 3d), along paths which pass away the distance piece (13) for the movable jaws (2, 2'), and which pass away the fixed jaws (3, 3') for the blade (4). This last feature has for its purpose to detach any paper ply which could remain gripped either to the movable jaws (2, 2') or to the blade (4).

Figure 5:
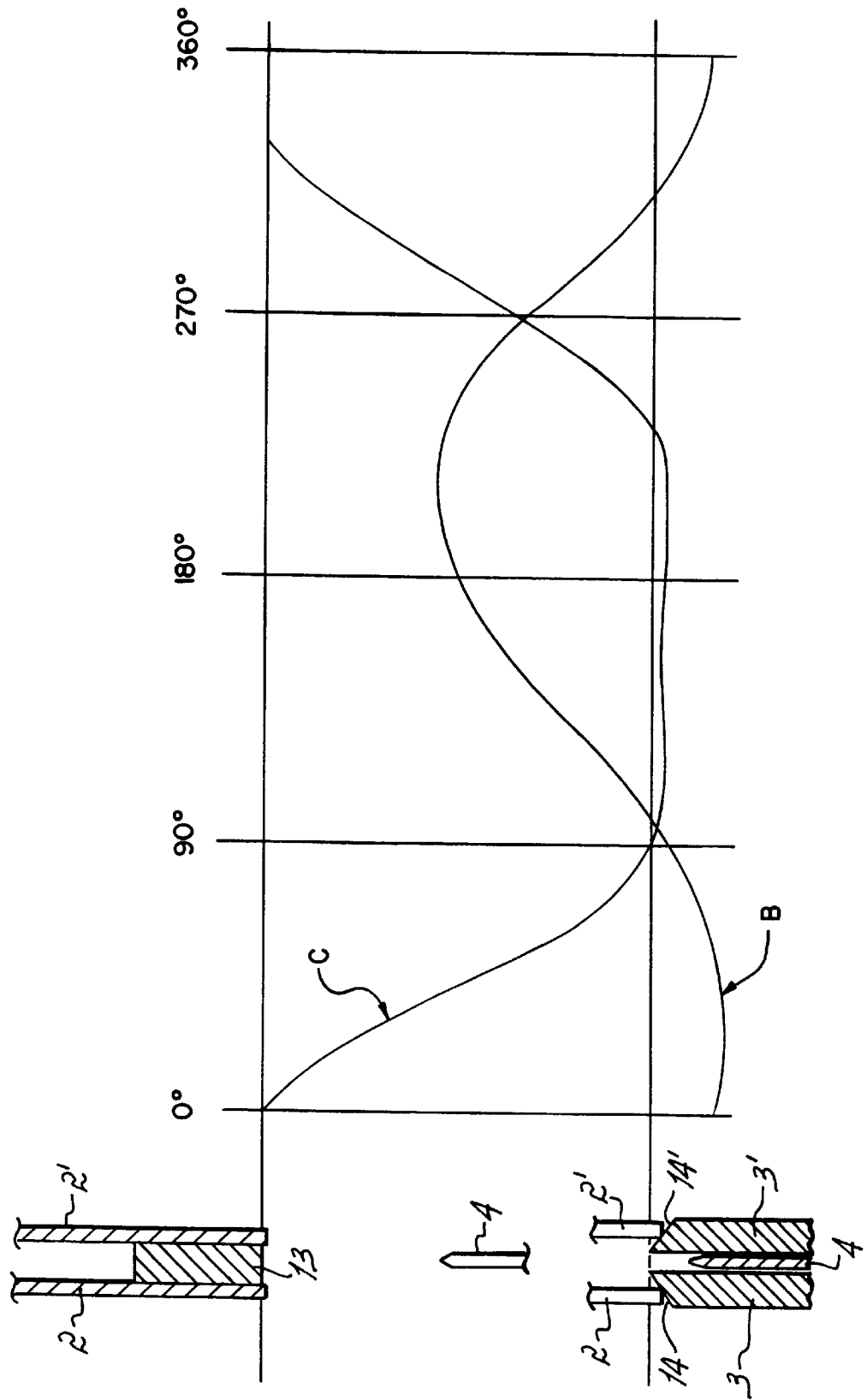
FIG. 5 is a running diagram showing the device kinematics, i.e. illustrating the relative positions of the immobilizing means and of the tearing means in the steps illustrated in FIGS. 3a to 3d.

The respective paths of the movable jaws (2, 2') and of the tearing and severing plate (4) are clearly described with their mutual relationship in FIG. 5, in which the curve (C) shows the path of the movable jaws (2, 2') and the curve (B) shows the path of the teeth-plate (4) during a full cycle of the device.

In this diagram, the movable jaws (2, 2') and the teeth-plate (4) are shown in full line, whereas they are also shown in their extreme positions, in thinner line. The curve (C) has a minimum flattened section corresponding to the period of time during which both pairs of jaws (2, 2', 3, 3') are engaged (slightly less than half a period of cycle).

The curve (B) is a quasi-sinusoid, which shows the regularity of the motion of the plate (4) with a maximum occurring obviously during the engagement of jaws (2, 2', 3, 3').

The maximum of curve (C) at the end of the cycle, therefore just before a next cycle, illustrates the feature mentioned above: the movable jaws (2, 2') move away after the distance piece (13) to detach if needed any ply of paper still gripped by the movable jaws (2, 2').

The same applies to the minimum of curve (B) which is well under the fixed jaws (3, 3') for the same reason applied to plate (4).

The band material in displacement along the axis (A) and severed by tearing off at its both ends, has a very specific configuration, of the pillow like type, in which the plies are flattened and intermingled at said ends, due to the very specific conditions of severing.

The device and machine of the invention provide therefore a product having a cohesion much higher than the products severed by a traditional cutting device using a shearing type operation.

What is claimed is:

1. In a machine for producing cushioning dunnage from a strip of stock material, the produced cushioning dunnage having a longitudinal axis, an assembly for separating a length of produced cushioning dunnage in two comprising:

a first pair of jaws positioned on one side of the cushioning dunnage and being fixed relative to said machine;

a second pair of jaws positioned on the side of the cushioning dunnage opposite from said first pair of jaws and being selectively movable relative to said first pair of jaws to clamp the cushioning dunnage between said first and second pairs of jaws;

a separating plate selectively movable between the respective jaws of said first and second pairs of jaws during clamping of the cushioning dunnage therebetween to separate the cushioning dunnage in two; and a drive mechanism for moving said second pair of jaws and said separating plate;

wherein said drive mechanism comprises:

a rotatable driving member;

a first linkage connected to said driving member and operably connected to said second pair of jaws; and a second linkage connected to said driving member and operably connected to said separating plate.

2. The machine of claim 1 wherein said driving member, first linkage and second linkage are operable to move said second pair of jaws in a first direction toward said first pair of jaws to clamp the cushioning dunnage therebetween and to move said separating plate in a second direction, opposite to the first direction, to separate the cushioning dunnage in two.

3. The machine of claim 1 wherein said driving member and first and second linkages move said second pair of jaws and said separating plate perpendicularly to the longitudinal axis of the cushioning dunnage.

4. The machine of claim 1 wherein said driving member is a disk.

5. The machine of claim 1 wherein said first linkage comprises:

a first link having a first end pivoted to said driving member;

a second link having a first end pivoted to said second pair of jaws; and a third link having a first end pivoted to the machine;

said first, second and third links having respective second ends pivoted together.

6. The machine of claim 1 wherein said second linkage comprises:

a first link having a first end pivoted to said driving member; and a second link having a first end pivoted to said separating plate;

said first and second links having respective second ends pivoted together;

said second link being pivoted to the machine intermediate said first and second ends of said second link.

7. The machine of claim 5 wherein said second linkage comprises:

a first link having a first end pivoted to said driving member; and a second link having a first end pivoted to said separating plate;

said first and second links having respective second ends pivoted together;

said second link being pivoted to the machine intermediate said first and second ends of said second link.

8. In a machine for producing cushioning dunnage from a strip of stock material, the produced cushioning dunnage having a longitudinal axis, an assembly for separating a length of produced cushioning dunnage in two comprising:

a first clamping member positioned on one side of the cushioning dunnage and being fixed relative to said machine;

a second clamping member positioned on the side of the cushioning dunnage opposite from said first clamping member and being selectively movable relative to said first clamping member to clamp the cushioning dunnage between said first and second clamping members;

a separating member selectively movable during clamping of the cushioning dunnage between said first and second clamping members to separate the cushioning dunnage in two; and a drive mechanism for moving said second clamping member and said separating member;

wherein said drive mechanism comprises:

a rotatable driving member;

a first linkage connected to said driving member and operably connected to said second clamping member; and a second linkage connected to said driving member and operably connected to said separating member.

9. The machine of claim 8 wherein said driving member, first linkage and second linkage are operable to move said second clamping member in a first direction toward said first clamping member to clamp the cushioning dunnage therebetween and to move said separating member in a second direction, opposite to the first direction, to separate the cushioning dunnage in two.

10. The machine of claim 8 wherein said driving member and first and second linkages move said second clamping member and said separating member perpendicularly to the longitudinal axis of the cushioning dunnage.

11. The machine of claim 8 wherein said driving member is a disk.

12. The machine of claim 8 wherein said first linkage comprises:

a first link having a first end pivoted to said driving member;

a second link having a first end pivoted to said second clamping member; and a third link having a first end pivoted to said machine;

said first, second and third links having respective second ends pivoted together.

13. The machine of claim 8 wherein said second linkage comprises:

a first link having a first end pivoted to said driving member; and a second link having a first end pivoted to said separating member;

said first and second links having respective second ends pivoted together;

said second link being pivoted to said machine intermediate said first and second ends of said second link.

14. The machine of claim 12 wherein said second linkage comprises:

a first link having a first end pivoted to said driving member; and a second link having a first end pivoted to said separating member;

said first and second links having respective second ends pivoted together;

said second link being pivoted to the machine intermediate said first and second ends of said second link.

* * * * *